US005955067A

United States Patent [19]

Oge et al.

[11] Patent Number: 5,955,067

[45] Date of Patent: Sep. 21, 1999

[54] POTASSIUM-CONTAINING COMPOSITION USEFUL IN THE TREATMENT OF ACNE, PSORIASIS AND SEBORRHEA

[76] Inventors: Eray Oge, 11 Clamshell La., Northport, N.Y. 11768; Gary Goodwin, 31 Brushwood Dr., Shirley, N.Y. 11967-4009

[21] Appl. No.: 08/685,137

[22] Filed: Jul. 23, 1996

[51] Int. Cl.[6] ................................ A61K 9/06; A61K 9/10

[52] U.S. Cl. ....................... 424/78.07; 424/610; 424/640; 424/642; 424/670; 424/679; 424/617; 424/715; 424/401; 514/859; 514/863; 514/864; 514/937; 514/944; 514/945; 514/887

[58] Field of Search .................................... 514/859, 863, 514/864, 937, 944, 945, 887; 424/610, 640, 642, 670, 679, 617, 715, 401, 78.07

[56] References Cited

PUBLICATIONS

Plewig G., and E. Schopf. (1975). Anti–Inflammatory Effects of Antimicrobial Agents : An In Vivo Study. *J. Invest. Dermatol.* 65(6) : 532–536.

*Primary Examiner*—Raj Bawa

[57] ABSTRACT

A composition is disclosed which is useful in alleviating, at least in part, symptoms of acne vulgaris, psoriasis or seborrhea, which includes a potassium-based compound a dermatologically acceptable base for the potassium-based compound, which is preferably a potassium salt, and which include potassium acetate, potassium aluminate, potassium arsenite solution, potassium bicarbonate, potassium bisulfate potassium bitartararte, potassium bromide, potassium carbonate, potassium chloride, potassium citrate, potassium gluconate, potassium glycerophosphate, potasium iodate, potassium iodide, potassium manganate, potassium permanganate, potassium phosphate monobasic potassium phosphate dibasic, potassium phosphate tribasic, potassium phosphite or a combination thereof. The composition is topically applied to the areas of a patient's skin which are afflicted with any of acne vulgaris, psoriasis or seborrhea.

2 Claims, No Drawings

POTASSIUM-CONTAINING COMPOSITION USEFUL IN THE TREATMENT OF ACNE, PSORIASIS AND SEBORRHEA

BACKGROUND OF THE INVENTION

1. Technical Field of the Invention

The present invention relates, generally to a composition containing potassium and its use for alleviating, at least in part, the symptons of acne, psoriasis and seborrhea, as well as a method for its use.

More particularly, the present invention relates to a composition containing potassium, which is applied topically to a person's skin in area afflicted with acne, psoriasis or seborrhea for the purpose of reducing the effects of such skin ailments.

2. Description of the Prior Art

Acne vulgaris is a common inflammatory pilosebaceous skin disease characterized by comedones, papules, pustules, inflamed nodules, superficial pus filled cysts and in extreme cases canalizing and deep inflamed sacks.

Thus far, there is no complete cure for acne vulgaris. The cleansing agents that contain keratolytic properties, such as sulfur and salicylic acid, may have some drying effect and are acceptable if tolerated. The most effective topical agents known to the medical arts are benzoyl peroxide and tretinoin (more commonly known by its trademark "RETIN A.") Topical use of certain antibiotics serve useful therapeutic adjunct. Systemic antibiotics have been tried with some success. Latest in acne treatment was the introduction of isoretinoin (more commonly known by the trademark "ACCUTANE.") The exact mechanism of action of ACCUTANE is not fully understood. Although introduction of ACCUTANE appeared to be a breakthrough in acne treatment, because of its risk of severe adverse effects of multi-system involvement, its use is limited and restricted to patients with severe cystic acne who do not responds to other conventional treatments.

Psoriasis is chronic, recurrent skin disease of unknown etiology transmitted autosomal dominant trait and characterized by sharply circumscribed scaly patches. There is no complete cure for psoriasis. The usual effective treatment includes topical use of salicylic acid, tars, anthralin compounds and corticostreoids. Latest in psoriasis treatment is the introduction of etratinate (trademark "TEGISON") systemically and calcipotrien (trademark "DOVONEX") topically.

The mechanism of action of TEGISON is unknown. This product is known to have the potential of causing severe adverse reactions, therefore its use is limited to severe cases of psoriasis which do not respond to other, more conventional, treatments.

Calcipotriene ointment ("DOVONEX ") is a synthetic derivative of vitamin D3. The controlled studies demonstrated that at least 70% of patients treated with Dovonex showed marked improvement after eight weeks of treatment. Although this product is highly effective in treatment of psoriasis, a transient and reversible elevation of serum calcium may occur during treatment, therefore, extreme precaution should be taken and if serum calcium elevation occurs, treatment should be discontinued until the serum calcium level returns to normal.

Seborrheic dermatitis is common inflammatory, scaly, crusting eruption, involving the body areas containing greatest concentration of sebaceous glands. The most effective topical agents so far are salicylic acid, tars, sulfur and corticosteroids.

There is a significant demand and need in the medical arts for an effective treatment in reducing the symptoms of acne vulgaris, psoriasis and seborrhea, which is substantially non-toxic to the vast majority of patients undergoing such a treatment.

Numerous treatments for acne, psoriasis or seborrhea have been provided in prior art that are adapted to be utilized. While these treatments may be suitable for the particular purpose to which they address, they would not be as suitable for the purposes of the present invention as heretofore described.

SUMMARY OF THE INVENTION

It is, therefore, an object of the present invention to provide an effective treatment for significantly reducing the symptoms of acne vulgaris, psoriasis and seborrhea, which would be non-toxic to the vast majority of patients suffering from any of the foregoing ailments.

It is a further object of the present invention to provide an effective treatment for significantly reducing the symptons of acne vulgaris, psoriasis and seborrhea, which is simple and inexpensive to formulate and may be used by a patient in an easy and convenient manner.

The foregoing and related objects are achieved by the present invention, which provides a potassium-containing composition for topical application to the areas of the skin of a patient which evidences the symptoms of any of acne vulgaris, psoriasis or seborrhea. The potassium-containing composition will generally be in the form of a potassium, such as potassium bromide (KBr), potassium chloride (KCl) or potassium iodide (KI.) A more complete listing of potassium-based compositions falling within the scope of the present invention will be provided hereinafter.

The potassium-containing composition of the present invention may be used by itself, may be contained in a liquid solution or may otherwise be incorporated into an emulsion, cream ointment, suspension or gel preparation, preferably containing 1–30% potassium by weight.

It is well known in the medical field that certain individuals, due to various medical surgical or neurological impairments lose their ability to receive oral feedings and therefore need to be fed through by other means, most commonly by use of a tube feeding. There are a number of ready made nutrient formulas available on the market for this purpose, which are formulated to contain essential nutrients to sustain life.

The inventors have made the surprising observation that patients receiving one particular tube feeding formula showed either complete clearence or significant improvement in the lesions of preexisting acne vulgaris, psoriasis or seborrheic dermatitis. This was a purely coincidental finding and observation.

The inventors then proceeded to study the various feeding tube formulae and, through further experimentation, discovered that the amount of potassium available in a particular feeding formula was the effective factor in bringing about, and correlated with, the above described finding and observation.

The inventors then proceeded to introduce similar doses of supplemental potassium orally and/or topically to otherwise healthy volunteers with various stages of acne, psoriasis and seborrheic dermatitis and observed complete clearence or significant improvement of the lesions existing prior to treatment. These individuals did not present any clinical or laboratory evidence of adverse reaction during or after the trial, by periodic assessments.

The potassium saturation treatment as an entity by itself, or an adjunct to other conventional treatments provides, a new modality to clinicians in the treatment of acne, psoriasis or seborrheic dermatitis. Potassium saturation treatment by topical route is safe. Although the cells and tissues are saturated locally at the site of application, significant absorption to blood stream is unlikely to occur so as to cause any systemic adverse effect.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

DETAILED DESCRIPTION OF THE PREFERRED EMBODIMENTS

Potassium (K) is an alkaline metallic element, occurring abundantly in nature, however, because of its high reactivity, always found in a chemical composition form, such as part of a salt. Its salts are largely used in medicine for therapeutic or intracellular fluid and is essential for maintenance of acid-base isotonicity, electrodynamic characteristic of the cell. Potassium is an important activator in many enzymatic reactions and is essential to a number of physiologic processes including transmission of nerve impulses; contracting of cardiac and smooth and skeletal muscles; gastric secration; renal function; tissue synthesis and carbohydrate metabolism. Once it is absorbed, potassium first enters the extracellular fluid and is then actively transported in the cells where its concentration is up to 40 times that outside of cells. In healty adults, plasma potassium concentration generally range from 3.5 to 5 mEq/L. Potassium is excreted mainly by kidneys; except for severe renal impairment, hyperkalemia or potassium toxicity is not likely to result from topical administration of potassium.

On the basis of the clinical observation described above, a trial was conducted by the inventors, whereby salts of potassium were administered by different routes to achieve potassium saturation of the cells and tissues which are involved in pathology of acne vulgaris, psoriasis or seborrheic dermatatis. The usual solvents, emulsifiers, bases, and vehicles, were used to facilitate intradermal absorbtion.

The present invention will now be described in greater detail by way of the following examples. It should, however, be recognized that the following examples are intended for the purpose of illustrating the formulation and use of certain preferred embodiments of the present invention and are not intended as a means for defining or limiting the scope thereof.

EXAMPLE NO. 1

Topical intradermic route:

Potassium Acetate ($KC_2H_3O_2$)

Potassium Aluminate ($K_2Al_2O_4$)

Potassium Arsenite Solution

Potassium Bicarbonate ($KHCO_3$)

Potassium Bisulfate ($KHSO_4$)

Potassium Bitartararte ($KC_4H_5O_6$)

Potassium Bromide (KBr)

Potassium Carbonate ($K_2CO_3$)

Potassium Chloride (KCl)

Potassium Citrate ($K_3C_6O_{7H}5$)

Potassium Gluconate ($KC_6O_7H_{11}$)

Potassium Glycerophosphate ($KC_3P_2O_6H_7$)

Potasium Iodate ($KIO_3$)

Potassium Iodide (KI)

Potassium Manganate ($KMnO_4$)

Potassium Permanganate ($K_2MnO_4$)

Potassium Phosphate Monobasic ($KH_2PO_4$)

Potassium Phosphate Dibasic ($K_2HPO_4$)

Potassium Phosphate Tribasic ($K_3PO_4$)

Potassium Phosphite ($K_2HPO_3$)

Any of the above listed salts of potassium by itself, or in combination are used to prepare the composition of the present invention as a liquid solution, emulsion, cream, ointment, suspension, mixture or gel preparation to contain 1% to 30% potassium. The repeated application of these preparations to the afflicted areas of the skin of a patient has provided potassium saturation of the cells and tissues locally, where the cells and tissues are involved in pathology of acne vulgaris, psoriasis or seborrheic dermatitis. Conventional solvents, emulsifiers, bases and vehicles are used to facilitate intradermal absorption. Addition of pertinent agents to augment the activity may be added, such as salicyclic acid for the acne embodiment of the inventions and coal tar for the psoriasis and seborrhea embodiments of the invention.

Examples of the most beneficial formulas known to the inventors are as follows:

| | | |
|---|---|---|
| A: Acne Vulgaris - | KCl 4.58% | Polysorbate 20.1% |
| | $KPO_4$ monobasic 2.06% | Propylene Glycol 1% |
| | $KPO_4$ dibasic 4.81% | Carboxymethylcellulose 1% |
| | Salicyclic acid 0.5% | Purified water 325 ml |
| | Magnesium Chloride 0.25% | |
| | Isopropyl Myristate 2.0% | |
| B: Psoriasis - | KCl 3.65% | MgCl 0.5% |
| | $KPO_4$ Monobasic 3.42% | Polysorbate 80 5.0% |
| | $KPO_4$ Dibasic 4.00% | Propylene Glycol 1% |
| | Coal Tar USP 0.5% | A&D Ointment USP 4 oz |
| C: Seborrhea Lotion - | KCl 3.65% | MgCl 0.5% |
| | $KPO_4$ Monobasic 3.42% | Polysorbate 80 5% |
| | $KPO_4$ Dibasic 4.00% | Propylene Glycol 1% |
| | Coal Tar USP 0.38% | Light Mineral oil |
| | USP 16.85% | in Purified Water |

Both B and C have contained vanillin 0.25% which has shown to be effective in masking any undesirable "tar" odor.

EXAMPLE NO. 2

Iontophoresis Route

Iontophoresis, also termed "ion transfer" is the introduction of substances into the body for therapeutic puposes by mean of direct current. The basis of successful ion transfer lies in the physics principle that like charged ions and subatomic matter repel, while oppositely charged particles attract. Ions being charged particles with positive or negative valances, are repelled into the skin by identical charge on the electrode surface placed over it. Each substance is seperated into ionic components by action of the currents and deposited subcutaneously, according to imposed polarity on the electrode. The following basic formula gives approximate grams of substance introduced:

$$I \times T \times (ECE) = \text{grams of substance introduced,}$$

wherein,

I is intensity;

T is time measured in hours; and,

ECE is electrochemical equivalency.

For this purpose absorbent material is soaked in 2% to 10% solution of potassium salts listed on the Example No 1. The absorbent material then placed on target area where the potassium ion will penetrate the skin to saturate the cells and tissues which are afflicted with the pathology of acne vulgaris, psoriasis or seborrheic dermatitis. The positive electrode is placed over absorbent material and secured inplace. Another absorbent material is soaked in distilled water and placed in a distant location as negative or indifferent electrode. The generator turned on and current gradually advanced until 5 mA is reached.

The duration of treatment will generally be between 20 to 30 minutes for each session. The treatment is repeated until the desired effect is achieved.

The clinical response time to potassium saturation treatment is different for each individual patient and depends upon the severety of the lesions. Typically some improvement is visible within 48 to 72 hours after initiation of treatment by any of the foregoing methods.

The exact mechanism of action "potassium saturation treatment" is not fully understood. However, potassium as being the major cation of the intracellular fluid plays an essential role of electro-dynamic characteristic of the cell, it is the activator of many enzymatic reactions and it is essential for tissue synthesis. Possibly, any one of these factors alone or in combination, might well play an important role in breaking the complex patho-physiological cycle of acne vulgaris, psoriasis and seborhheic dermatitis.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. The composition "for the treatment of acne vulgaris, psoriasis or seborrhea" consisting essentially of the following components in an aqueous base:

about 4.58 wt % potassium chloride
about 2.06 wt % potassium phosphate monobasic
about 4.81 wt % potassium phosphate dibasic
about 0.5 wt % salicylic acid
about 0.25 wt % magnesium chloride
about 2.0 wt % isopropyl myristate
about 1 wt % polysorbate 20
about 1 wt % propylene glycol and
about 1 wt % carboxymethylcellulose.

2. The composition "for the treatment of acne vulgaris, psoriasis or seborrhea" consisting essentially of the following components in an A&D ointment base:

about 3.65 wt % potassium chloride
about 3.42 wt % potassium phosphate monobasic
about 4 wt % potassium phosphate dibasic
about 0.5 wt % coal tar USP
about 0.5 wt % magnesium chloride
about 5 wt % polysorbate 80 and
about 1 wt % propylene glycol.

* * * * *